United States Patent [19]

Dory

[11] Patent Number: 5,354,258
[45] Date of Patent: Oct. 11, 1994

[54] ULTRA-HIGH-SPEED EXTRACORPOREAL ULTRASOUND HYPERTHERMIA TREATMENT METHOD

[75] Inventor: Jacques Dory, Coupvray, France

[73] Assignee: EDAP International, Marne la Vallee, France

[21] Appl. No.: 1,988

[22] Filed: Jan. 7, 1993

[30] Foreign Application Priority Data

Jan. 7, 1992 [FR] France .................. 92 00051

[51] Int. Cl.$^5$ .............................................. A61B 5/00
[52] U.S. Cl. .......................................... 601/3; 607/97
[58] Field of Search ........ 128/660.03, 24 EL, 24 AA; 607/97, 101, 102

[56] References Cited

U.S. PATENT DOCUMENTS

| 3,735,755 | 5/1973 | Eggleton et al. . | |
| 4,757,820 | 7/1988 | Itoh | 128/24 AA |
| 4,955,365 | 9/1990 | Fry et al. | 128/24 AA |
| 5,143,074 | 9/1992 | Dory . | |
| 5,150,711 | 9/1992 | Dory . | |

FOREIGN PATENT DOCUMENTS

| 370841 | 5/1990 | France . |
| 2664819 | 1/1992 | France . |
| 820814 | 9/1959 | United Kingdom . |

Primary Examiner—Ruth S. Smith
Attorney, Agent, or Firm—Welsh & Katz, Ltd.

[57] ABSTRACT

An extracorporeal ultra-high-speed ultrasound hyperthermia treatment method consisting in transmitting and focussing on the tumor ultrasound wave trains at frequencies between 0.5 and 10 MHz with peak electric powers which may reach 20 Kw or more, the parameters which define the concentration of the treatment beam in the focal spot and the power being determined so that, irrespective of the depth and the nature of the tissue, the treatment time is in the order of that enabling significant destruction, preferably total destruction, of the target during the linear part of a curve showing the temperature increase as a function of time.

12 Claims, 5 Drawing Sheets

| F | k | dT/sec |
|---|---|---|
| .5 | 71.15 | 26.85 |
| 1 | 90 | 33.97 |
| 1.5 | 64.03 | 24.17 |
| 2 | 35.99 | 13.58 |
| 2.5 | 17.78 | 6.71 |
| 3 | 8.09 | 3.05 |
| 3.5 | 3.48 | 1.31 |
| 4 | 1.43 | .54 |
| 4.5 | .57 | .21 |
| 5 | .22 | .08 |
| 5.5 | .08 | .03 |
| 6 | .03 | .01 |
| 6.5 | .01 | 0 |
| 7 | 0 | 0 |
| 7.5 | 0 | 0 |
| 8 | 0 | 0 |
| 8.5 | 0 | 0 |
| 9 | 0 | 0 |
| 9.5 | 0 | 0 |
| 10 | 0 | 0 |

FIG. 3b

| F | k | dT/sec |
|---|---|---|
| .5 | 4.25 | 71.45 |
| 1 | 14.33 | 240.49 |
| 1.5 | 27.13 | 455.28 |
| 2 | 40.59 | 681.01 |
| 2.5 | 53.37 | 895.32 |
| 3 | 64.66 | 1084.77 |
| 3.5 | 74.05 | 1242.32 |
| 4 | 81.38 | 1365.27 |
| 4.5 | 86.66 | 1453.86 |
| 5 | 90.02 | 1510.21 |
| 5.5 | 91.65 | 1537.53 |
| 6 | 91.77 | 1539.57 |
| 6.5 | 90.62 | 1520.28 |
| 7 | 88.43 | 1483.52 |
| 7.5 | 85.41 | 1432.91 |
| 8 | 81.77 | 1371.76 |
| 8.5 | 77.67 | 1302.97 |
| 9 | 73.26 | 1229.09 |
| 9.5 | 68.68 | 1152.24 |
| 10 | 64.03 | 1074.23 |

ULTRA-HIGH-SPEED EXTRACORPOREAL ULTRASOUND HYPERTHERMIA TREATMENT METHOD

BACKGROUND OF THE INVENTION

1. Field of the invention

The present invention concerns an ultra-high-speed extracorporeal ultrasound hyperthermia method and treatment device.

2. Description of the prior art

It is known, in particular from RE 33,590, to use a focussed ultrasound beam to cause extremely localized heating of biological tissue in order to destroy tumors. The beam is transmitted in the form of periodic wave trains having a predetermined frequency peak power and duration.

In the device described in the patent referred to above, the beam high frequency ranges between 0.5 and 5 MHz, for example, the lower frequencies being used to destroy the deeper structures within the body and the electric peak power which excites the transducer is comparatively low (10 to 100 watts, the higher powers being used to destroy the deeper structures).

These wave trains, the duration of each of which is about 1 second, are separated by intervals of about 1/10 second during which it is possible to carry out real time (usually type B) ultrasound scanning to relocate the focus relative to the target (which is affected by natural movements of the tissues caused by breathing) or to examine the damage sustained by the tissues in the treated area.

With the power level and frequencies employed—which depend on the depth of the target area—the target temperature is increased to approximately 45° C., a temperature which is sufficiently high in principle to destroy malignant cells. It has been thought previously that an excessive increase in the temperature of the target area could cause serious burns in the surrounding area as the result of thermal diffusion.

As a result, treatment times are relatively long, possibly several tens of minutes or even several hours.

The invention is based on the discovery that increasing the peak power of the waves used by a factor of 10 to 200 or more, depending on the depth and the absorbing power of the target area, makes it possible, by causing an ultra-high-speed temperature rise, to significantly reduce the effects of thermal diffusion and to destroy the target area in time periods in the order of one second or less.

SUMMARY OF THE INVENTION

It is an object of the invention to provide a method of effecting an ultra-high-speed treatment of a region of a subject located at a known depth within the body with compressional wave energy derived from ultrasonic transducer means for applying to said region a focussed beam transmitted in the form of periodic bursts of oscillations having a predetermined frequency and a predetermined peak power, each burst having a predetermined duration and the successive burst being separated by time intervals, said method including the steps of:

effecting tests with said ultrasonic transducer means on a target located at said depth within the body for determining the curve of temperature increase of said target as a function of the time of application of said compressional wave energy, said time curve having a quasi-linear portion which starts at time zero and ends at a time $t_o$;

determining the particular peak power of said burst of oscillations which will provide at least a substantial destruction of said region of the subject in a single burst of oscillations having a duration equal to the time $t_o$ and selecting a peak power of treatment at least equal to said particular peak power and a duration of the treatment burst at most equal to the time $t_o$.

It is another object of the invention to provide a method of the type above referred to, in which the frequency as well as the diameter of the transmitting surface of the ultrasonic transducer means and the diameter of the focal spot are advantageously determined and selected according to the nature and depth of the target so that the concentration of the beam is maximized and the power is then determined for a selected value of the frequency and of the selected diameters so that the target is destroyed at a temperature much larger than that which was generally used in prior art and in a time period much shorter.

Tests effected by the applicant have shown that the construction of the device which implements this method, requiring the implementation of means for quasi-continuous transmission of compressional wave energy at very high peak powers, can minmize the destruction of healthy cells whilst enhancing the effectiveness with which the target is destroyed, in particular as the result of an additional mechanical destructive effect on the cells of the target, so providing a new localized ultrasound hyperthermia treatment technique justifying subsequent use in this description of the term "ultra-high-speed hyperthermia treatment".

According to another aspect of the invention, the ultra-high-speed hyperthermia treatment method provides significantly improved echographic examination of changes to the target during treatment.

Therefore, it is a further object of the invention to provide a method of ultra-high-speed hyperthermia treatment in which the examination of the target is carried out by type A or B echography during interruptions in the treatment beam at a given rate such that the A echogram or the B image has time to undergo detectable modifications (which could mean a few tenths of a second in ultra-high-speed hyperthermia treatment) which are not masked by spurious modifications caused by movements of the wave trains (as is the case in practice with prior art hyperthermia treatment techniques).

The invention also has for its object specific type A or B echographic methods which facilitate the ultra-high-speed detection of change sustained by the target so that treatment can be terminated as soon as the target is destroyed.

Other features and the advantages of the invention will be more clearly apparent from the following description in which the ultra-high-speed echographic detection methods are described first, to facilitate the subsequent description of the treatment method and of the construction of the specific features of the ultra-high-speed hyperthermia treatment device.

DETAILED DESCRIPTION OF THE INVENTION

Figure 1:
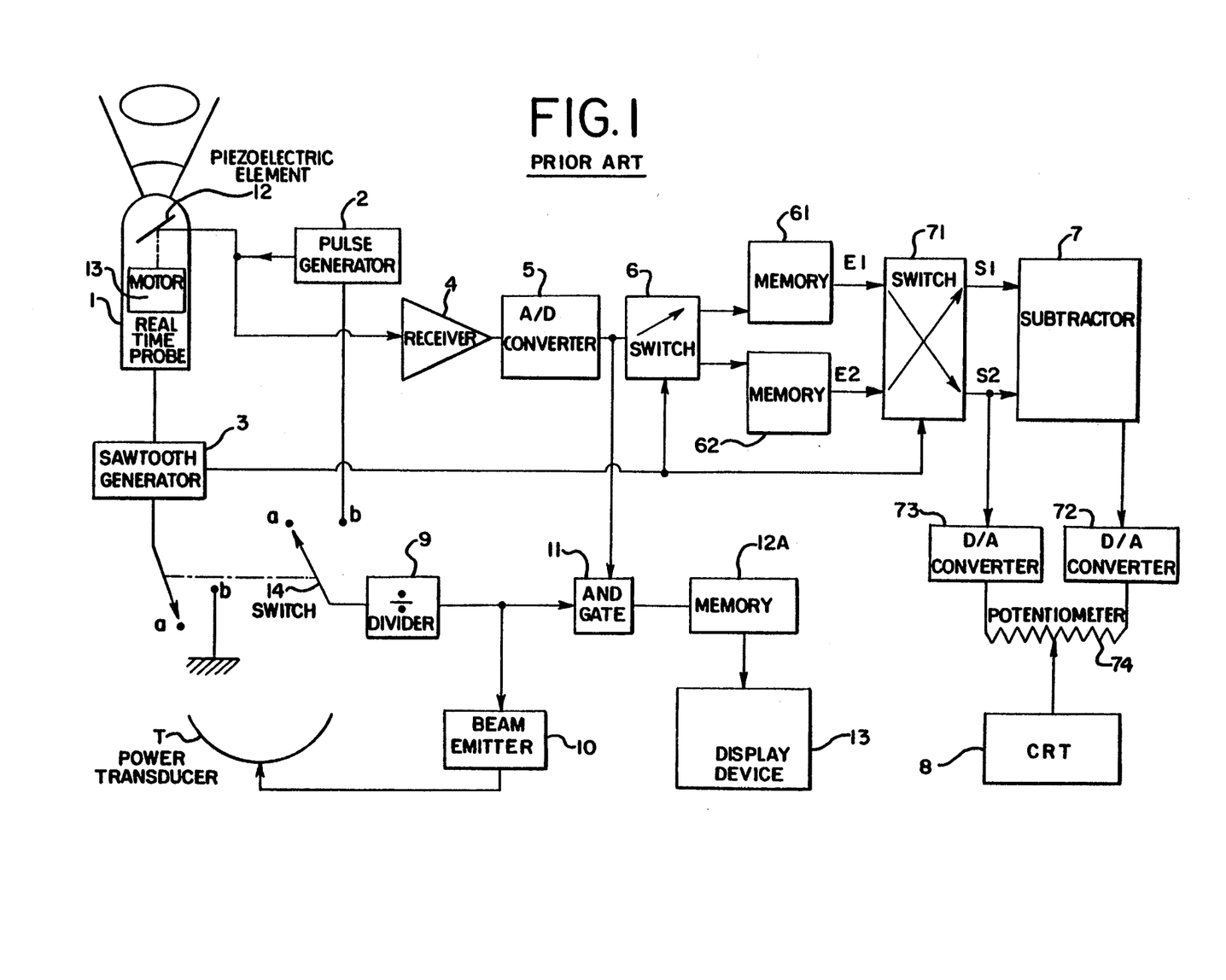
FIG. 1 is a block diagram showing an ultra-high-speed hyperthermia treatment device provided with means for ultra-high-speed detection of change to the target during treatment.

FIG. 1 is a block diagram of a known type echography device comprising a real time probe 1 including a piezoelectric transducer element 12 which is oscillated by an electric motor 13 through a mechanical transmission system represented by the chain-dotted line.

For example, this probe may be as described in U.S. Pat. No. 4,418,698 granted Dec. 6, 1983 in respect of: "Mechanical sector scanned echographic probe".

Figure 2:
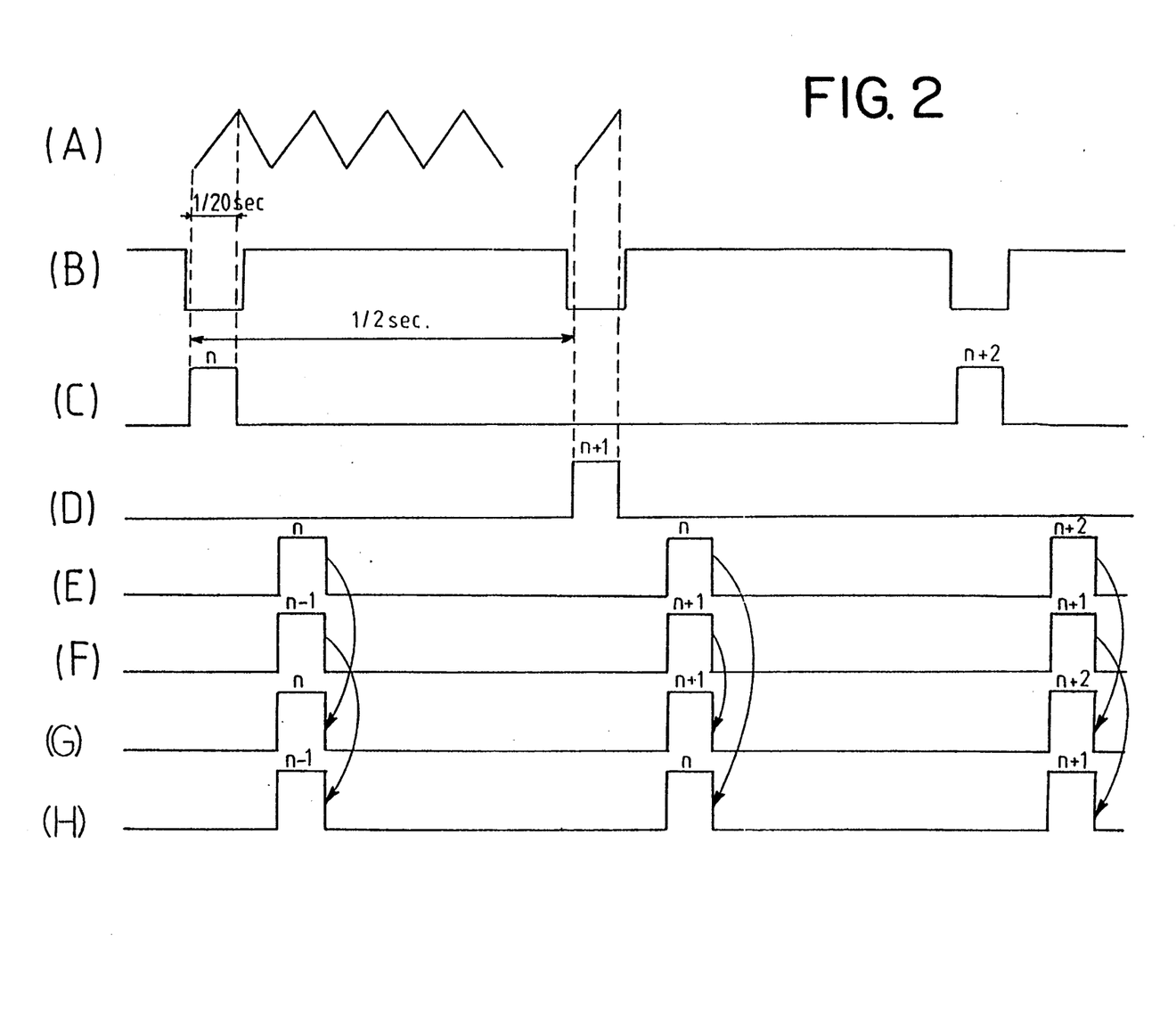
FIG. 2 is a timing diagram showing the operation of said detection means.

The piezo-electric element 12 is excited by a pulse generator 2 and the motor is controlled by a sawtooth scanning signal generator (producing the waveform (A) shown in FIG. 2) to scan a sector of the region to be treated, the scan passing through the focus of the treatment beam emitter.

The echo pulses reflected from biological structures are amplified by a receiver 4 whose output is connected to an analog-to-digital converter 5.

An electronic switch 6 connects the output of the converter 5 to one or other of two memories 61 and 62. Switching occurs on each scan, the switch 6 being connected to an appropriate output of the sawtooth generator 3 for this purpose.

In each memory, addressing of the writing operation is effected in a known manner according to the angular position of the beam emitted by the probe and the time elapsed since the start of each pulse transmission, so that a complete image of the treated area is written into one of the two memories on each scan.

The memories are also read in a known way and the resulting signals are fed to a digital subtractor 7 through a switch 71 which reverses the connection between its inputs E1 and E2 and its outputs S1 and S2 on each scan (being connected to the appropriate output of the generator 3 to this end).

If no inversion were applied, the subtractor, which computes the difference between the serial digits which define the successive points of the two images, would subtract the current image from the previous image and then the previous image from the current image, and so on, the inversion being required so that the previous image is always subtracted from the current image in each scan.

The output of the subtractor 7 is connected to a digital-to-analog converter 72 which supplies a voltage for modulating the brightness of the cathode ray tube of a display device 8.

The output S2 is connected to a second digital-to-analog converter 73. A potentiometer 74 provides a variable mix of the output voltage of the converter 72, representing the differential image, and the output voltage of the converter 73, representing the latest image stored.

The operator can then observe either the conventional image of the treated area, enabling a preliminary identification of the structures concerned, or the differential image, enabling him to observe how the structures change during the treatment.

As the treatment uses extremely high peak powers, the images cannot be formed during emission of the treatment beam, the energy of which, reflected from the structures concerned, is sufficient to "dazzle" the echographic transducer. The effect of this can continue for one or more microseconds after the end of emission. It is therefore necessary to emit wave trains separated by gaps (waveform (B) in FIG. 2) slightly longer than the duration of an echographic scan, which might be 1/20 s, for example, and to synchronize the latter with the emission.

It is obviously also necessary for the images to be formed at a sufficiently high rate for natural movement of the tissue as a result of breathing not to introduce excessive differences between two successive images, which would mask the differential effect resulting from the modification of the structures due to the treatment. To give an example, the emission time could be chosen to obtain an image every 0.5 s at least. This implies that the peak power of the treatment emission be sufficient for significant destruction of the target area cells to occur in a few tenths of a second.

FIG. 2 shows at (C) the intervals in which the memory 61 is written, at (D) the intervals in which the memory 62 is written, at (E) the intervals in which the memory 61 is read, at (F) the intervals in which the memory 62 is read and at (G) and (H) the resulting states of the outputs S1 and S2. The numbers of the images in memory are shown. This shows that the previous image is always subtracted from the current image.

Referring again to FIG. 1, the power transducer T, symbolically represented as a spherical cup on which piezo-electric elements are placed, is energized by the treatment beam emitter 10. The transducer is advantageously as described in RE 35,590 and the probe 1, although shown separately, would in practice be attached to the cup, disposed at its center and oriented along its axis, as explained in the aforementioned patent.

FIG. 1 also shows units that are not used in the embodiment of the invention described thus far, but only in a modified embodiment now to be described.

These units are a variable ratio frequency divider 9, an AND gate 11, a memory 12a, a display device 13 and a switch 14.

When the switch 14 is in position a, the divider 9 is connected to the sawtooth generator 3, which is adapted to provide a synchronization signal when the axis of the probe passes through the focus of the treatment beam emitter (the center of the sphere of which the cup T constitutes a portion). The division ratio of the divider is then set to a value between 1 and 5, for example.

It therefore provides every N scans a short signal applied to the power emitter 10 and which disables it for its duration of approximately 1 ms.

The short signal is also applied to the gate 11 which is therefore enabled for 1 ms and passes to the memory 12a the digital signal from the converter 5.

The memory 12a has the time to acquire information representing a scanning line, the duration of which is in the order of only 0.2 ms (as compared with 0.2 to 0.02 s to acquire a complete image).

Thus in this modified embodiment the treatment beam will be interrupted for one ms during the duration of the treatment beam pulses, and this will occur every 1/20 s, for example, resulting in only a very slight reduction (2% for example) of the mean power as compared with an uninterrupted treatment beam.

The line acquired "on the fly" in this way, every 1 to 5 scans, passes through the focus. This method finally uses a type A echography, and the information collected in one direction only is sufficient. An equivalent result could be obtained by immobilizing the probe in a particular direction through the target.

The echo signals stored in the memory 12a are read out at a rate of 50 Hz, for example, and displayed continuously on the screen of the device 13.

This reading frequency promotes visual comfort.

In this modified method, the eye of the operator performs the equivalent of the digital subtraction of the information collected during treatment, at a rate such that it can perceive changes in the amplitude of the ultrasound scan.

It should be understood that using a type B ultrasound probe to obtain type A echograms has the advantage of enabling the same probe to be used for type B ultrasound scanning before a target is treated (here the term "target" refers to a part of the tumor which is exactly the same size as the focal spot, and complete treatment of the tumor will entail focussing the beam onto the various target areas constituting it in succession), to locate said target area as described in the previously mentioned RE 33,590. A relocation can even be carried out by the same probe for type B ultrasound scanning during the treatment of a target, by interrupting the treatment beam for a sufficient time to obtain an image (1/20 s).

The ultra-high-speed hyperthermia treatment method will now be explained with reference to FIGS. 3a, 3b, 4 and 5.

Figure 3A:
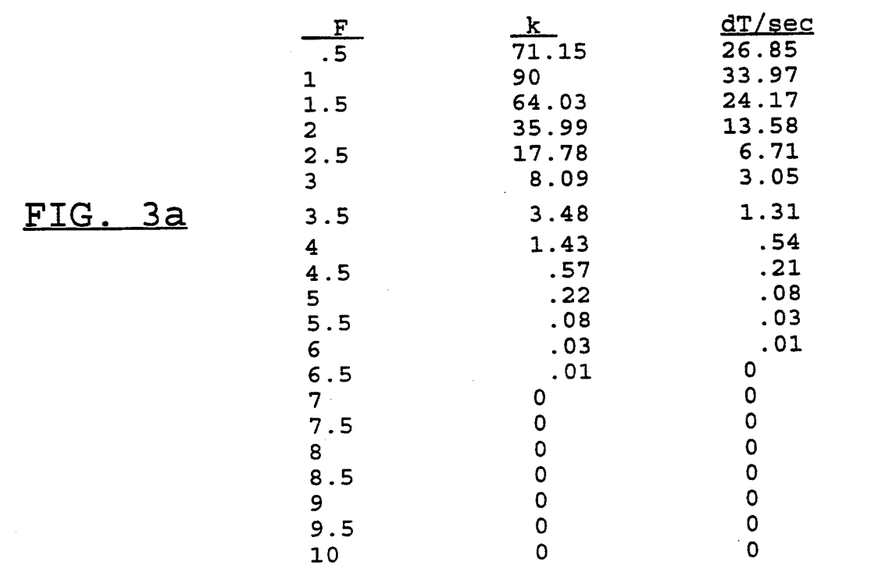
FIGS. 3a and 3b illustrate tables indicating the global concentration k and the rate dT/sec of temperature rise as a function of frequency F, for given characteristic parameters of the transducer means.

The table illustrated in FIG. 3a corresponds to a power transducer T having a spherical transmitting surface, with a focal distance of 10 cm and an aperture angle of 60° of the beam.

The values of the global concentration factor k, where $k = k_a \times k_g$, have been calculated by the applicant for a power transducer shaped as a spherical cup having a given first diameter D and producing a focal spot having a given second diameter d. The geometrical concentration factor $k_g$ is defined as D/d and represents the concentration of energy due to the geometric shape of the transducer. The attenuation factor $k_a$, is known experimental data and represents the attenuation of acoustic waves in a biological tissue other than a bone or a tissue which contains air. The attenuation factor, $k_a$, is about 1 dB per MHz per cm of propagation path within the tissue.

The rate dT/sec. of a temperature rise as a function of frequency F has been calculated, for a given diameter d of the focal spot and a given entry diameter of the beam into the body, for an aperture constant angle of the beam and a transmitted acoustic peak power of 1 Kw, by making the assumption that the energy losses in the tissue which are due to absorption amount to 1% of the transmitted power, other losses, amounting to 9% of the transmitted power, being bound to multiple reflection upon the cell surfaces. Thus, one has been able to calculate the fraction of the power losses which is absorbed and is converted into heat within the tissue and therefore, the rate of temperature rise.

It should be noted that available prior art data generally indicate absorption losses higher than 1% (for instance between 2-3%). It therefore results from the assumption made by the applicants that the calculated ratio of temperature rise is most probably lower than that which will actually be obtained. This may lead to an overevaluation of the calculated peak power required, but overevaluation is better than underevaluation, which would lead to an increased risk of thermal diffusion in the tissues surrounding the target.

Figure 3B:
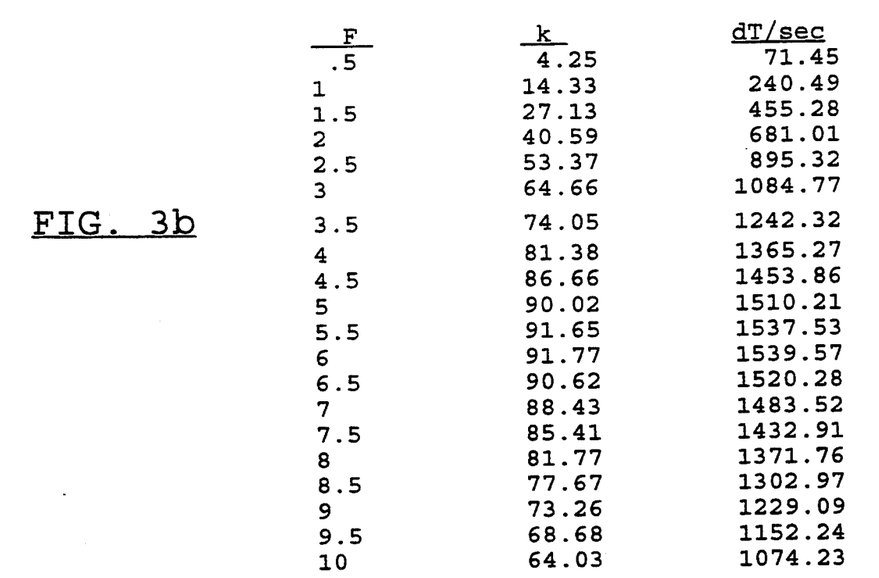

FIG. 3a corresponds to a focal length of 10 cm and an entry diameter of 10 cm, whereas FIG. 3b corresponds to a focal length of 1.5 cm and an entry diameter of 1.5 cm.

The operating frequency F will be selected as follows: First, the focal length which is nearer from the depth of the target within the body (i.e. the distance along the beam path between skin and tumor) will be selected.

As an example; for a target depth of about 10 cm, a focal length of 10 cm will be selected and therefore, the table of FIG. 3a will be used for frequency calculation.

The selected frequency will be that which both corresponds to the maximum value of k and to the maximum rate of temperature rise. FIG. 3a shows that F=1 Mhz.

For a focal length of 1.5 cm (which will be selected for tumors of small depth), the table of FIG. 3b shows that the selected frequency will be 6 MHz.

It should be noted that the above method of selecting the optimal operating frequency is based on the hypothesis that thermal diffusion and cooling of the tissue, due to blood circulation, are negligibly small, these phenomena not having been taken into account in the applicant's calculations.

In fact, these phenomena could have—if the applicants's method were not used—a very important effect when a heat source of small volume, as a focal spot of 1.5 mm of diameter is used. However, as the applicant's method effects heating only during the quasi-linear part of the curve of temperature increase as a function of the heating time, it finally results that nearly the whole of the energy which is absorbed by the target is used for heating it and therefore, the losses due to the above mentioned phenomena are actually negligibly small with respect to the absorbed power.

Figure 4:
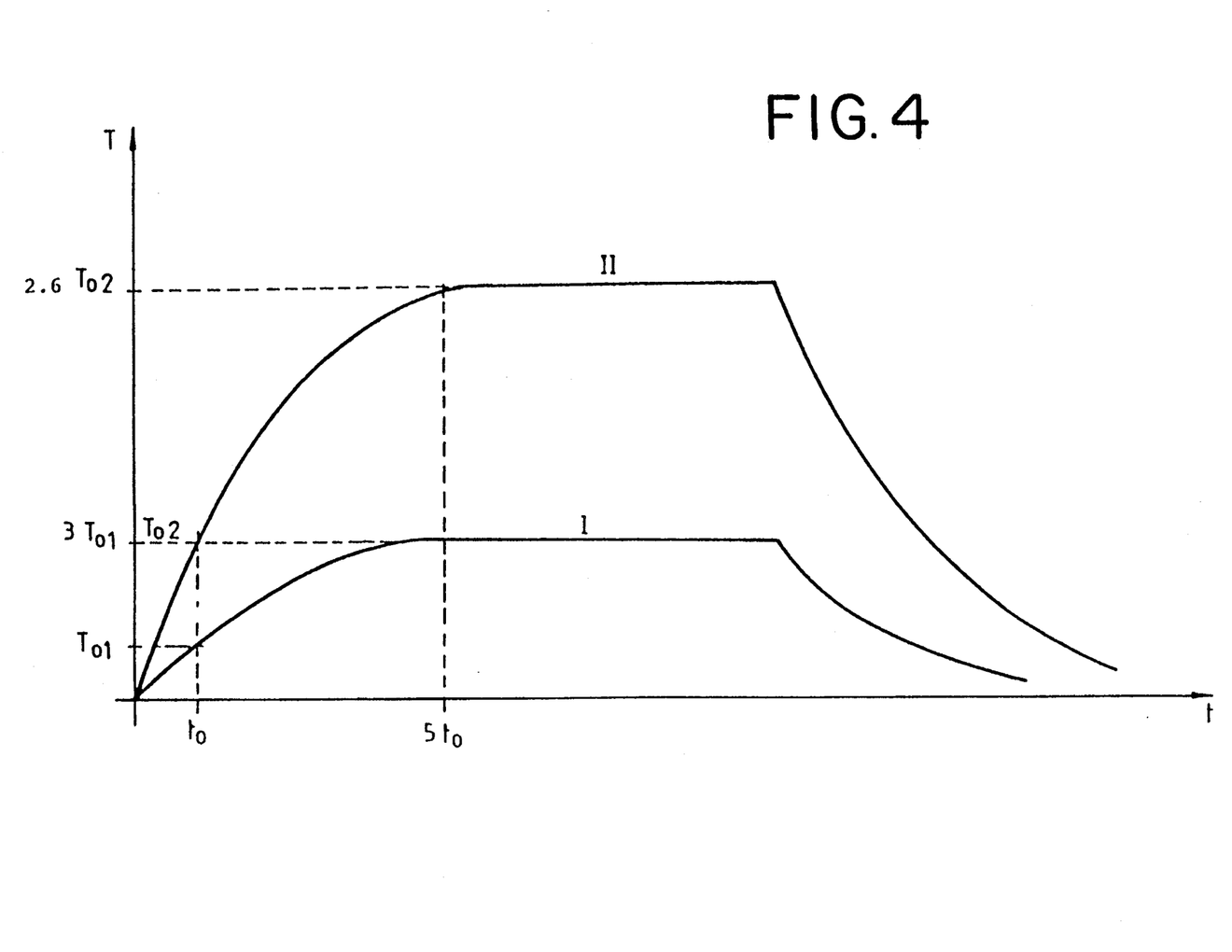
FIG. 4 shows curves representing the temperature increase of a biological tissue as a function of heating time.

The curves of FIG. 4 show, for a small heat source (in this example a small diameter focal spot), the experimentally determined increase in the temperature T of the area acted on by an ultrasound beam as a function of the application time, for two different applied power levels (curves II and II).

The temperature rise is seen to be quasi-linear over a time $t_o$ which is substantially the same for both curves, but corresponds to different temperatures, respectively $T_{o1}$ and $T_{o2}$. After a ceiling which corresponds to an equality between the thermal losses and the supply of heat, and which is reached after a time of 5 $t_o$ and corresponds to a temperature of about 3 $T_{o1}$ for curve I and 2.6 $T_{o2}$ for curve II, the temperature T then rapidly decreases.

Note that $t_o$ is independent of the applied power and is in direct proprotion to the focal spot diameter. In the experiments yielding the curves shown in FIG. 4, the frequency is 1 MHz, the focal spot diameter is 1.5 mm and $t_o$=0.5 s. The applicant has determined similar curves from tests carried out for various values of the operating frequency and of the focal spot diameter, in particular for the values which are indicated in the tables.

The applicant's method, consisting in selecting a peak power such that a total or at least a substantial destruction of the target cells will be obtained after a time of $t_o$ at most, it will result, according to the applicant's discovery, that minimal damage will be caused to tissues in the area surrounding the target.

It further results that the total quantity of heat energy required by the method for destroying the target is much smaller than in prior art methods.

These experimental results can be explained by the fact that, in the linear region of the curve, losses by diffusion are negligible in comparison with the heat input. Beyond this point, the losses are proportional to the temperature gradient between the target and the surrounding tissue, and so increase rapidly until they are equal to the heat input (at the ceiling temperature). When the input of heat is terminated, the temperature of the target decreases exponentially to a value at which there is substantially no more destruction after a time in the order of 3 to $6 \times t_o$ in these experiments. This time (in the order of 1.5 to 3 s in this case) will substantially define the minimum gap between two successive wave trains of the treatment wave, so that all wave trains are subject to minimal losses by diffusion.

However, in practice, it has been found that a preferred value of the gap is at least ten times the wave train duration.

In FIG. 2, where the wave train duration is sligthly less than 0.5 s, a value chosen because it corresponds to $t_o$, the successive wave trains, separated by only 0.05 s, will be applied to different targets in the tumor, a single wave train being sufficient to compare the reflective state of each target before and after it is applied.

Figure 5:
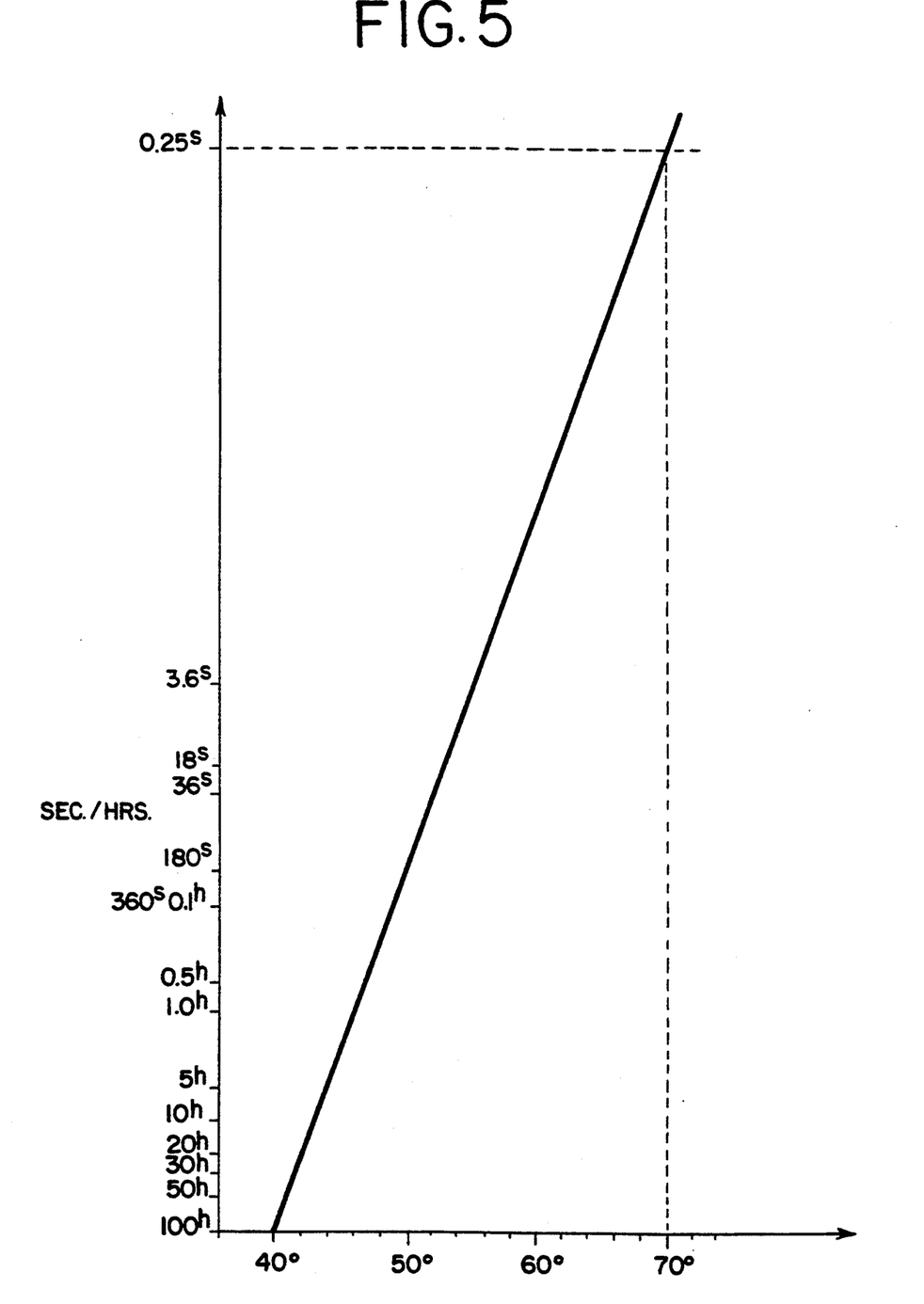
FIG. 5 is a graph illustrating the time of destruction of a biological tissue as a function of the heating temperature.

It is known that the time t to destroy tumor cells is inversely proportional to the temperature T to which they are subjected from a threshold value $T_i$ of the latter which is 40° C., for example. For T=58° C., the graph of FIG. 5 shows that the value of t is in the order of 0.5 s. The application time t is substantially halved for each increase in temperature of 10° C. above 43° C., so that it is divided by 4096 on increasing from 58° C. to 70° C., for example.

It should be noted that, as the tissues will be destroyed in 0.5 seconds only if the temperature of 58° has been reached in a time substantially lower than 0.5 s. The duration of the treatment burst equalling half of the time $t_o$ indicated by the graph of FIG. 5 will preferably be selected. Therefore, a value of $0.5 \times t_o = 0.25$ s will be selected. A temperature of 70° C. will then be reached at the end of the power burst, i.e. in 0.25 s.

The table of FIG. 3a shows that dT/sec=33.97 for an acoustic peak of 1 Kw. Therefore, to raise the target temperature approximately 32° C. above normal in 0.25 s, representing a rate of temperature increase of 128° C./s, the power should be multiplied by the ratio 128/33.97=4, it being obvious that the rate of temperature rise is substantially proportional to the heating power when one operates in the quasi-linear part of the curve.

The factor of power conversion of the transducer T being about ¼, and account being taken of the transmission losses along the path of the beam, an electric peak power of about between 10 to 20 Kw shall finally be used.

With the view of avoiding too large a power density on the piezoelectric transducer element which comprises transducer T, the latter will consist of a spherical cap having for instance a diameter of 300 mm and a focal length of 300 mm with an aperture angle of 60°.

Selection of such a focal length results from a compromise between the required condition that the aperture angle should be as large as possible so as to concentrate acoustic energy at the focus and the requirement that the entry surface of the beam within the body should be comparatively small, for avoiding an interference of the beam with bones, air pockets or other obstacles to the propagation of ultrasounds.

In a practical embodiment, as the focal length of the apparatus will not be variable, the operator will displace the transducer for bringing it to a distance from the skin equalling the target depth, thus obtaining coincidence between the target and the focal spot.

The attenuation of ultrasounds in the coupling water medium being negligibly small, the tables of FIGS. 3a and 3b remain valid.

A single apparatus, having a maximum electric peak power of 20 Kw, and the power of which is controllable, and having a wave train duration which may be varied between 0.01 and 1 s for instance, will enable the practician to treat targets of any depth ranging from a few cm to 10–12 cm. A graph will be provided by the manufacturer to indicate the optimal duration of the wave train for each tumor, as a function of its depth.

The power may be adjusted, it being understood that the deeper tumors will require the maximum power.

However, it might be preferred to manufacture three different devices for treating three respective ranges of target depths.

For example, for an emitted power of 1 Kw, respective focal lengths of 10 and 12 cm and respective tissue entry diameters of 10 and 12 cm, the optimum frequency determined from the tables is 1 Mhz, yielding temperature increase rates of 33.97° C./s and 21.43° C./s respectively. An electric power of 20 Kw will then be used as explained hereinabove.

For focal lengths of 3 and 5 cm and respective entry diameters of 3 and 5 cm, the respective optimal frequencies will be 3 and 1.5 MHz and the respective rates of temperature increase will be 384.89° C./s and 135.91 C./s. Powers of between 2 and 5 Kw will then for instance be used.

For a focal length of 1.5 cm, the optimum frequency will be 6 MHz and the temperature increase will be 539.57° C., requiring in practice a power level in the order of 1 Kw and typically between one hundred to one thousand watts.

Generally speaking, the peak powers used in ultrahigh-speed hyperthermia treatment, especially to treat deep tumors, require that special provisions are embodied in the construction of the device. In particular, it is necessary to use piezo-electric ceramic materials capable of supporting such high peak powers and of cooling quickly. Forced cooling arrangements may be needed. The supply of power to the electrical generator may require the use of auxiliary power supplies.

Note that the optimum power values specified should not be significantly exceeded, to avoid the risk of lesions affecting the surrounding tissue. It has been shown that the diameter of the area within which the temperature rise resulting from the diffusion of heat energy accumulated in the focal region at the moment when application of power is terminated remains sufficiently high to destroy the cells relatively quickly increases in proportion to the square root of the temperature increase in the focal region, which increase is in turn proportional to the power.

Finally, note that at the powers indicated the ultrasound beam is progressively transformed to a significant degree during its propatation, the result being the appearance of thermic components at higher frequencies than those of the original beam.

These high frequency components are more strongly absorbed by the tissue and therefore have greater thermal effect. Moreover, experiments made by the applicant have shown that the risk of burning the skin is decreased.

The frequencies and powers chosen enable the beam to pass with little damage through the outer layers of tissue and to produce a thermal effect at the focal spot.

The beam additionally has a mechanical effect which complements its thermal effect for increased treatment efficiency.

What is claimed is:

1. A method of effecting an ultra-high-speed hyperthermia treatment of a region of a subject located at a known depth within the body, with compressional wave energy derived from ultrasonic transducer means for applying to said region a focussed beam transmitted in the form of periodic bursts of oscillations having a predetermined frequency and a predetermined peak power, each burst having a predetermined duration and the successive bursts being separated by time intervals, said method comprising the steps of:
    a) effecting tests with said ultrasonic transducer means on a target located at said depth within the body for determining the curve of temperature increase of said target as a function of the time of application of said compressional wave energy, said curve having a quasi-linear portion which starts at time zero and ends at a time $t_o$;
    b) determining the particular peak power of said burst of oscillations which will provide at least a substantial destruction of said region of the subject in a single burst of oscillations having a duration equal to the time $t_o$; and
    c) selecting a peak power of treatment at least equal to said particular peak power and a duration of the treatment bursts at most equal to the time $t_o$.

2. The method of claim 1, wherein said frequency is adjusted to be about equal to 1 Mhz and an electric peak power is adjusted such that at least 10 Kw is applied to said ultrasonic transducer means.

3. The method of claim 1, wherein said frequency is adjusted to be between 1.5 and 3 Mhz and an electric peak power adjusted to be between 2 Kw and 5 Kw is applied to said ultrasonic transducer means.

4. The method of claim 1, wherein said frequency is adjusted to be about equal to 6 Mhz and an electric peak power adjusted to be about between 100 to 1000 watts is applied to said ultrasonic transducer means.

5. The method of claim 1, wherein said frequency is adjusted to be about equal to 1 Mhz and an electric power peak adjusted to range between 10 to 20 Kw is applied to said ultrasonic transducer means.

6. The method of claim 1, wherein said duration is adjusted to be between 0.5 and 3 seconds.

7. The method of claim 1, wherein said duration is adjusted to be between 0.01 and 1 second.

8. The method of claim 1, wherein said intervals are adjusted to each equal at least ten times said duration.

9. The method of claim 1, wherein said duration is adjusted to be about equal to one half of the time $t_o$.

10. The method of claim 1, wherein said transducer means has a predetermined focal length, a circular transmitting surface and a circular focal spot having first and second predetermined respective diameters, said method comprising the further steps of:
    d) calculating, as a function of said frequencies and for a plurality of different focal lengths and a peak power of said compressional wave energy equalling 1 Kw, tables of the global concentration factor, k, of the focused beam, where $k = k_a \times k_g$, $k_a$ being the attenuation factor of the compressional wave energy along the beam path between said transmitting surface and said focal spot and $k_g$ being the ratio between said first and second diameters;
    e) selecting from said plurality of different focal lengths the focal length value which is nearer from the depth of said region and, for said nearer value, selecting from the table the maximum value of said global concentration factor, said maximum value corresponding in the table to a particular frequency;
    f) selecting a frequency of treatment substantially equalling said particular frequency.

11. The method of claim 10, wherein said tables further comprise calculated values of the temperature rise per unit of time of a region of a subject to which said compressional wave energy is applied and said method comprises the further steps of:
    g) determining on the basis of different values of the time of lethal exposure of animal or human living tissues to heat, as a function of the temperature which said tissues are brought to, the value of the temperature rise per unit of time to which the tissues should be subjected for destroying them in the duration of the treatment burst which has been selected in step c); and
    h) calculating the ratio between the value of the temperature rise per unit of time which has been calculated in step g) and the value of the temperature rise per unit of time which is given by the table for the focal length selected in step e) and the particular frequency selected in step f) and wherein the determination of the particular peak power is step b) is carried out by multiplying 1 Kw by the ratio calculated in step h).

12. The method of claim 10, wherein said transmission surface is selected to have a diameter of 300 mm, said focal spot is selected to have a diameter of 1.5 mm, said focal distance is selected to be 300 mm and said path is selected to have an aperture angle of 60°.

* * * * *